(12) United States Patent
Peters et al.

(10) Patent No.: US 7,662,808 B2
(45) Date of Patent: Feb. 16, 2010

(54) DIAZABICYCLIC ARYL DERIVATIVES AS CHOLINERGIC RECEPTOR MODULATORS

(75) Inventors: Dan Peters, Ballerup (DK); Gunnar M. Olsen, Ballerup (DK); Elsebet Østergaard Nielsen, Ballerup (DK); Tino Dyhring Jørgensen, Ballerup (DK); Daniel B Timmermann, Ballerup (DK)

(73) Assignee: NeuroSearch A/S, Ballerup (DK)

( * ) Notice: Subject to any disclaimer, the term of this patent is extended or adjusted under 35 U.S.C. 154(b) by 367 days.

(21) Appl. No.: 10/586,836

(22) PCT Filed: Feb. 1, 2005

(86) PCT No.: PCT/EP2005/050404

§ 371 (c)(1),
(2), (4) Date: Jul. 21, 2006

(87) PCT Pub. No.: WO2005/074940

PCT Pub. Date: Aug. 18, 2005

(65) Prior Publication Data

US 2008/0227773 A1  Sep. 18, 2008

Related U.S. Application Data

(60) Provisional application No. 60/541,753, filed on Feb. 5, 2004, provisional application No. 60/573,347, filed on May 24, 2004.

(30) Foreign Application Priority Data

Feb. 4, 2004 (DK) ................................ 2004 00171
May 24, 2004 (DK) ................................ 2004 00812

(51) Int. Cl.
  *A01N 43/00*   (2006.01)
  *A61K 31/33*   (2006.01)
  *C07D 487/00*  (2006.01)
(52) U.S. Cl. ...................................... 514/183; 540/471
(58) Field of Classification Search ........................ None
   See application file for complete search history.

(56) References Cited

U.S. PATENT DOCUMENTS

| 5,478,939 A | 12/1995 | Trybulski et al. |
| 6,407,095 B1 | 6/2002 | Lochead et al. |
| 6,635,645 B1 | 10/2003 | Lochead et al. |
| 7,067,507 B2 * | 6/2006 | Pulley et al. ................. 514/183 |
| 2003/0114461 A1 | 6/2003 | Galli et al. |
| 2003/0153574 A1 | 8/2003 | Galli et al. |
| 2004/0029884 A1 | 2/2004 | Gallet et al. |
| 2004/0266757 A1 | 12/2004 | Galli et al. |
| 2005/0004258 A1 | 1/2005 | Yamamoto et al. |
| 2005/0020599 A1 | 1/2005 | Galli et al. |

FOREIGN PATENT DOCUMENTS

| EP | 1 219 622 A2 | 7/2002 |
| WO | WO-99/42465 A | 8/1999 |
| WO | WO-00/34279 A | 6/2000 |
| WO | WO-00/34284 A1 | 6/2000 |
| WO | WO-00/44755 A1 | 8/2000 |
| WO | WO-01/92259 A | 12/2001 |
| WO | WO-01/92260 A1 | 12/2001 |
| WO | WO-01/92261 A | 12/2001 |
| WO | WO-03/044019 A | 5/2003 |
| WO | WO-03/044020 A | 5/2003 |
| WO | WO-03/044024 A | 5/2003 |
| WO | WO-2004/024729 A1 | 3/2004 |
| WO | WO-2004/029053 A1 | 4/2004 |

OTHER PUBLICATIONS

Decker et al. Expert Opinion in Investigational Drugs, 2001, 10(10), 1819-1830.*
"Biogenic amines", http://www.nlm.nih.gov/cgi/mesh/2008/MB_cgi?mode=&index=14697&field=all&HM=&ll=&PA=&form=&input=, accessed Dec. 12, 2008, PDF attached.*
"Receptors, Cholinergic", http://www.nlm.nih.gov/cgi/mesh/2008/MB_cgi?mode=&index=11477&field=all&HM=&ll=&PA=&form=&input=, accessed Dec. 12, 2008.*
"Central Nervous System Diseases", http://www.nlm.nih.gov/cgi/mesh/2008/MB_cgi, accessed Dec. 12. 2008.*
Wood et al. Expert Opinion in Investigational Drugs, 2002, 11(4), 457-67.*

* cited by examiner

*Primary Examiner*—James O Wilson
*Assistant Examiner*—Noble Jarrell
(74) *Attorney, Agent, or Firm*—Birch, Stewart, Kolasch & Birch, LLP

(57) ABSTRACT

This invention relates to novel diazabicyclic aryl derivatives which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemicals substances.

4 Claims, No Drawings

DIAZABICYCLIC ARYL DERIVATIVES AS CHOLINERGIC RECEPTOR MODULATORS

TECHNICAL FIELD

This application is the national phase of PCT application PCT/EP2005/050404 filed on Feb. 1, 2005 and claims priority under 35 U.S.C. 119(e) on U.S. Provisional Application No(s). 60/541,753 and 60/573,347 filed on Feb. 5, 2004 and May 24, 2004; respectively and under 35 U.S.C. 119(a) on Patent Application No(s). PA 2004 00171 and PA 2004 00812 filed in Denmark on Feb. 4, 2004 and May 24, 2004, all of which are hereby incorporated by reference.

This invention relates to novel diazabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

U.S. Pat. No. 5,478,939 (American Cyanamid) and WO 00/34284 (Sanofi-Synthelabo) both describe 2,5-diazabicyclo[2.2.1]heptane derivatives having affinity for nicotinic receptors.

WO 00/34279, WO 01/92259, WO 01/92260 and WO 01/92261 (Sanofi-Synthelabo), describe 1,4-diazabicyclo[3.3.2]nonane derivatives having affinity for nicotinic receptors.

WO 00/44755 (Abbott) describes diazabicyclic derivatives useful as nicotinic acetylcholine receptor ligands.

WO 99/42465 discloses diazabicyclo derivatives for use as serotonin Reuptake inhibitors, and EP 1219622 discloses diazabicyclic derivatives having activity at nicotinic receptors.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diazabicyclic aryl derivatives represented by Formula I

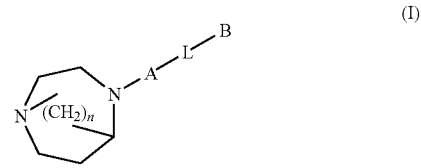

any of its enantiomers or any mixture of its enantiomers, or a pharmaceutically acceptable salt thereof, wherein n is 1, 2 or 3;

A represents a phenyl, a thiadiazolyl, a pyridyl or a pyridazinyl group;

B represents a phenyl group, a thiadiazolyl group, a pyridyl group or a pyridazinyl group; which aromatic group may optionally be substituted one or more times with substituents selected from the group consisting of $C_{1-6}$-alkyl, $C_{3-7}$-cycloalkyl, hydroxy, $C_{1-6}$-alkoxy, cyano-$C_{1-6}$-alkyl, halo, trihalo-$C_{1-6}$-alkyl, trihalo-$C_{1-6}$-alkoxy, cyano, amino, nitro, and —NH(CO)R''''; wherein R'''' represents hydrogen, $C_{1-6}$-alkyl or $C_{3-7}$-cycloalkyl; and L represents —O—, —S—, —S—CH$_2$—, —SO—, —C≡C—, —NHCO—, —NHCONH— or —NH(SO$_2$)—.

In its second aspect the invention provides pharmaceutical compositions comprising a therapeutically effective amount of the diazabicyclic aryl derivative of the invention, or a pharmaceutically-acceptable addition salt thereof, together with at least one pharmaceutically-acceptable carrier or diluent.

In a further aspect the invention relates to the use of the diazabicyclic aryl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

Other objects of the invention will be apparent to the person skilled in the art from the following detailed description and examples.

DETAILED DISCLOSURE OF THE INVENTION

Diazabicyclic Aryl Derivative

In a first aspect novel diazabicyclic aryl derivatives are provided. The diazabicyclic aryl derivatives of the Invention may be represented by the general Formula I

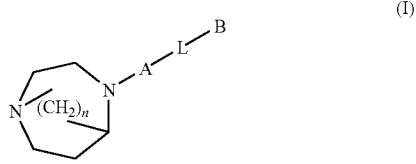

(I)

any of its enantiomers or any mixture of its enantiomers, or a pharmaceutically acceptable salt thereof, wherein n is 1, 2 or 3;

A represents a phenyl, a thiadiazolyl, a pyridyl or a pyridazinyl group;

B represents a phenyl group, a thiadiazolyl group, a pyridyl group or a pyridazinyl group; which aromatic group may optionally be substituted one or more times with substituents selected from the group consisting of $C_{1-6}$-alkyl, $C_{3-7}$-cycloalkyl, hydroxy, $C_{1-6}$-alkoxy, cyano-$C_{1-6}$-alkyl, halo, trihalo-$C_{1-6}$-alkyl, trihalo-$C_{1-6}$-alkoxy, cyano, amino, nitro, and —NH(CO)R""; wherein R"" represents hydrogen, $C_{1-6}$-alkyl or $C_{3-7}$-cycloalkyl; and L represents. —O—, —S—, —S—CH$_2$—, —SO—, —C≡C—, —NHCO—, —NHCONH— or —NH(SO$_2$)—.

In a preferred embodiment the diazabicyclic aryl derivative of the invention is a compound of Formula I wherein is 1 or 2. In a more preferred embodiment n is 2.

In another preferred embodiment the diazabicyclic aryl derivative of the invention is a compound of Formula I wherein A represents a phenyl group.

In a third preferred embodiment the diazabicyclic aryl derivative of the invention is a compound of Formula I wherein A represents a thiadiazolyl group.

In a most preferred embodiment the diazabicyclic aryl derivative of the invention is a compound of Formula I wherein A represents a phenyl, a thiadiazolyl, a pyridyl or pyridazinyl group.

In a fourth preferred embodiment B represents a phenyl group, a thiadiazolyl group, a pyridyl group or a pyridazinyl group; which aromatic group may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R""; wherein R"" represents hydrogen, alkyl or cycloalkyl.

In a fifth preferred embodiment B represents a phenyl group, a thiadiazolyl group, a pyridyl group or a pyridazinyl group; which aromatic group may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl.

In a sixth preferred embodiment B represents a phenyl group or a pyridyl group; which aromatic group may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl.

In a seventh preferred embodiment the diazabicyclic aryl derivative of the invention is a compound of Formula I wherein L represents —O—, —S—, —S—CH$_2$—, —SO—, —C≡C—, —NHCO—, —NHCONH— or NH(SO$_2$)—.

In a more preferred embodiment L represents —O—, —S—, —S—CH$_2$—, —SO—, —C≡C—, —NHCO— or —NHCONH—.

In an eighth embodiment the diazabicyclic aryl derivative of the invention is a compound of Formula I wherein n is 2; A represents phenyl, thiadiazolyl, pyridyl or pyridazinyl; B represents a phenyl or pyridyl group, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH$_2$—, —SO—, —C≡C—, —NHCO—, —NHCONH— or —NH(SO$_2$)—.

In an even more preferred embodiment n is 2; A represents phenyl; B represents a phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH$_2$—, —SO—, —C≡C—, —NHCO—, —NHCONH— or —NH(SO$_2$)—.

In a most preferred embodiment the diazabicyclic aryl derivative of the invention is N-[4-(1,4-Diaza-bicyclo[3.2.2]non-4-yl)-phenyl]-benzamide;

1-[4-(1,4-Diaza-bicyclo[3.2.2]non-4-yl)phenyl]-3-phenylurea;

N-[4-(1,4-Diaza-bicyclo[3.2.2]nonyl)-phenyl]-2-nitro-benzamide;

N-[4-(1,4-Diazabicyclo[3.2.2]non-4-yl)-phenyl]-3-nitro-benzamide;

N-[4-(1,4-Diaza-bicyclo[3.2.2]non-4-yl)-phenyl]-4-nitro-benzamide;

2-Amino-N-[4-(1,4-diaza-bicyclo[3.2.2]non-4-yl)-phenyl]-benzamide;

3-Amino-N-[4-(1,4-diaza-bicyclo[3.2.2]non-4-yl)-phenyl]-benzamide;

4-Amino-N-[4-(1,4-diaza-bicyclo[3.2.2]non-4-yl)phenyl] benzamide;

2-Acetylamino-N-[4-(1,4-diaza-bicyclo[3.2.2]non-4-yl) phenyl]-benzamide;

3-Acetylamino-N-[4-(1,4-diaza-bicyclo[3.2.2]non-4-yl)-phenyl]-benzamide;

4-Acetylamino-N-[4-(1,4-diaza-bicyclo[3.2.2]non-4-yl)-phenyl]-benzamide;

N-[4-(1,4-Diaza-bicyclo[3.2.2]non-4-yl)-phenyl]-3-methoxy-benzamide;

N-[4-(1,4-Diaza-bicyclo[3.2.2]non-4-yl)-phenyl]-benzenesulfonamide;

N-[4-(1,4-Diaza-bicyclo[3.2.2]non-4-yl)-phenyl]-4-methoxy-benzamide;

N-[4-(1,4-Diaza-bicyclo[3.2.2]nonyl)-phenyl]-3-cyano-benzamide;

N-[4-(1,4-Diaza-bicyclo[3.2.2]non yl)-phenyl]-4-cyano-benzamide;

N-[4-(1,4-Diaza-bicyclo[3.2.2]non-4-yl)-phenyl]-3-fluoro-benzamide;

N-[4-(1,4-Diaza-bicyclo[3.2.2]non-4-yl)-phenyl]-4-fluoro-benzamide;

N-[4-(1,4-Diaza-bicyclo[3.2.2]non-4-yl)-phenyl]2-fluoro-benzamide;

N-[4-(1,4-Diaza-bicyclo[3.2.2]non-4-yl)phenyl]-4-nitro-benzenesulfonamide; or

4-Amino-N-[4-(1,4-diaza-bicyclo[3.2.2]non-4-yl)-phenyl]-benzenesulfonamide;

or an enantiomers or a mixture of its enantiomers, or a pharmaceutically acceptable salt thereof.

In a ninth embodiment the diazabicyclic aryl derivative is a compound of Formula I wherein n is 2; A represents thiadiazolyl, pyridyl or pyridazinyl; B represents phenyl or pyridyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH$_2$—, —SO—, —C≡C—, —NHCO—, —NH-CONH— or —NH(SO$_2$)—.

In a more preferred embodiment n is 2; A represents thiadiazolyl; B represents phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH$_2$—, —SO—, —C≡C—, —NHCO—, —NHCONH— or NH(SO$_2$)—.

In an even more preferred embodiment A represents thiadiazolyl.

In a tenth preferred embodiment B represents phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl.

In an eleventh preferred embodiment L represents —O—, —S—, —S—CH$_2$—, —SO—, —C≡C—, —NHCO—, —NHCONH— or NH(SO$_2$)—.

In a most preferred embodiment the diazabicyclic aryl derivative of the invention is 4-(5-Benzylsulfanyl-[1.3.4]-thiadiazol-3-yl)-1,4-diaza-bicyclo[3.2.2]nonane;

or an enantiomers or a mixture of its enantiomers, or a pharmaceutically acceptable salt thereof.

In a twelfth preferred embodiment A represents pyridyl or pyridazinyl.

In a most preferred embodiment the diazabicyclic aryl derivative of the invention is 4-(6-Phenylethynyl-pyridazin-3-yl)-1,4-diaza-bicyclo[3.2.2]nonane;

4-[6-(4-Amino-phenylethynyl)-pyridazin-3-yl]-1,4-diaza-bicyclo[3.2.2]nonane;

4-[6-(3-Fluoro-phenylethynyl)-pyridazin-3-yl]-1,4-diaza-bicyclo[3.2.2]nonane;

4-[6-(4-Methoxy-phenylethynyl)-pyridazin-3-yl]-1,4-diaza-bicyclo[3.2.2]nonane;

4-[6-(3-Pyridinylethynyl)-pyridazin-3-yl]-1,4-diaza-bicyclo[3.2.2]nonane;

4-(6-Phenylsulfanyl-pyridazin-3-yl-1,4-diaza-bicyclo[3.2.2]nonane;

4-(6-Phenylsulfanyl-pyridazin-3-yl)-1,4-diaza-bicyclo[3.2.2]nonane;

4-(6-Phenoxy-pyridazin-3-yl)-1,4-diaza-bicyclo[3.2.2]nonane;

1-[6-(1,4-Diaza-bicyclo[3.2.2]non-4-yl)-pyridin-3-yl]-3-(2-nitro-phenyl)-urea-1-N-oxide;

N-[6-(1,4-Diaza-bicyclo[3.2.2]non-4-yl)-pyridin-3-yl]-benzamide;

1-[6-(1,4-Diaz-bicyclo[3.2.2]nonyl)pyridin-3-yl]-3-phenyl-urea;

N-[6-(1,4-Diaza-bicyclo[3.2.2]non-4-yl)-pyridin-3-yl]-4-nitro-benzamide;

N-[6-(1,4-Diaza-bicyclo[3.2.2]non-4-yl)-pyridin-3-yl]-3-nitro-benzamide;

4-Amino-N-[6-(1,4-diaza-bicyclo[3.2.2]non-4-yl)-pyridin-3-yl]-benzamide;

3-Amino-N-[6-(1,4-diaza-bicyclo[3.2.2]non-4-yl)-pyridin-3-yl]-benzamide;

4-Acetylamino-N-[6-(1,4-diaza-bicyclo[3.2.2]nonyl)-pyridin-3-yl]benzamide;

3-Acetylamino-N-[6-(1,4-diaza-bicyclo[3.2.2]non-4-yl)-pyridin-3-yl]benzamide;

N-[6-(1,4-Diaza-bicyclo[3.2.2]non-4-yl)-pyridin-3-yl]-3-methoxy-benzamide;

N-[6-(1,4-Diaza-bicyclo[3.2.2]non-4-yl)-pyridin-3-yl]-3-cyano-benzamide; or

N-[6-(1,4-Diaza-bicyclo[3.2.2]non-4-yl)-pyridin-3-yl]-4-cyano-benzamide;

or an enantiomers or a mixture of its enantiomers, or a pharmaceutically acceptable salt thereof.

Any combination of two or more of the embodiments described herein is considered within the scope of the present invention.

Definition of Substituents

In the context of this invention halo represents a fluorine, a chlorine, a bromine or an iodine atom. Thus, a trihalomethyl group represents e.g. a trifluoromethyl group, a trichloromethyl group and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention an alkoxy group designates an "alkyl-O—" group, wherein alkyl is as defined above. Examples of preferred alkoxy groups of the invention include methoxy and ethoxy.

In the context of this invention a cyanoalkyl group designates an "-alkyl-CN" group, wherein alkyl is as defined above.

Pharmaceutically Acceptable Salts

The diazabicyclic aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Particularly preferred onium salts of the invention include those created at the N' position according to the following formula I'

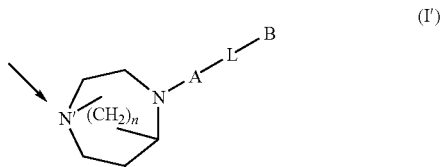

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Diazabicyclic Aryl Derivatives

The diazabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

The compounds of the present invention may in particular be agonists, partial agonists, antagonists and/or allosteric modulators of the nicotinic acetylcholine receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of diazabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulphate was used as drying agent in the workup-procedures and solvents were evaporated under reduced pressure.

1,4-Diazabicyclo[3.2.2]nonane (Intermediate Compound)

The title compound was prepared according to *J. Med. Chem.* 1993 36 2311-2320 (and according to a slightly modified method below).

1,4-Diazabicyclo[3.2.2]nonane (Intermediate Compound)

To the solution of 1,4-diazabicyclo[3.2.2]nonan-3-one (15.8 g; 113 mmol) in absolute dioxane (130 ml) $LiAlH_4$ (4.9 g; 130 mmol) was added under argon. The mixture was refluxed for 6 h and then allowed to reach room temperature. To the reaction mixture water (5 ml in 10 ml of dioxane) was added by drops, the mixture was stirred for 0.5 hour and then filtered off via glass filter. The solvent was evaporated and the residue was distilled using Kugelrohr apparatus at 90° C. (0.1 mbar) to yield 1,4-diazabicyclo[3.2.2]nonane (11.1 g; 78%) as colourless hygroscopic material.

1,4-Diazabicyclo[3.2.2]nonan-3-one (Intermediate Compound)

To the solution of 3-quinuclidinone hydrochloride (45 g; 278 mmol) in 90 ml of water hydroxylamine hydrochloride (21 g; 302 mmol) and sodium acetate ($CH_3COOHx3H_2O$; 83 g; 610 mmol), were added, the mixture was stirred at 70° C. for 1 hour and then cooled to 0° C. The separated crystalline material was filtered off (without washing) and dried in vacuo to yield 40.0 g of oxime.

The 3-quinuclidinone oxime (40.0 g) was added during 2 hours by small portions to preheated to 120° C. polyphosphoric acid* (190 g). The temperature of the solution during the reaction was kept at 130° C. After addition of all oxime the solution was stirred for 20 minutes at the same temperature, then transferred to an enameled vessel and allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated and the solid residue dried up in vacuo to yield 30.0 g (77%) of the mixture of lactams.

Crystallization of the obtained mixture from 1,4-dioxane (220 ml) gave 15.8 g (40.5%) of 1,4-diazabicyclo[3.2.2] nonan-3-one as colourless large crystals with mp. 211-212° C.

The filtrate was evaporated and the residue was chromatographed on a silica gel (Merck, 9385, 230-400 mesh) column with acetone as eluent. The solvent was evaporated and the residue recrystallized from ethyl etanoate to yield 1,3-diazabicyclo[3.2.2]nonan-4-one (10.2 g; 26%) as colourless fine crystals with mp. 125-126° C.

Polyphosphoric Acid*

85% Orthophosphoric acid (500 g; 294 ml; 4.337 mol) was placed into 2000 ml flask and then phosphor pentoxide (750 g; 5.284 mol) was added at room temperature (ratio acid-pentoxide, 2:3). The mixture was stirred at 200-220° C. for 2 hours to yield of 1250 g of polyphosphoric acid, containing 80% of $P_2O_5$.

Method A (Intermediate Compounds)

4-(6-Bromo-pyridazin-3-yl)-1,4-diazabicyclo[3.2.2]nonane fumaric acid salt

A mixture of 3,6-dibromo-pyridazine (3.77 g; 15.85 mmol) 1,4-diazabicyclo[3.2.2]nonane (2.00 g; 15.85 mmol) and aqueous sodium hydroxide (10 ml; 4M) was stirred at 100° C. for 30 minutes. The mixture was extracted with dichloromethane (3×20 ml). Chromatography on silica gel with dichloromethane, 10% methanol and 1% aqueous ammonia as solvent gave the title compound as an oil. Yield 0.88 g (20%). The corresponding salt was obtained by addition of a diethyl ether and methanol mixture (9:1) saturated with fumaric acid. Mp. 164.6-168.9° C.

4-(6-Chloro-pyridazin-3-yl)-1,4-diazabicyclo[3.2.2]nonane free base

The title compound was prepared according to Method A. Mp. 127.0-128.5° C.

Method B 4-(6-Phenylethynyl-pyridazin-3-yl)-1,4-diaza-bicyclo[3.2.2]nonane fumaric acid salt (Compound B1)

A mixture of 4-(6-bromo-pyridazin-3-yl)-1,4-diazabicyclo[3.2.2]nonane (1.0 g; 3.5 mmol), phenylacetylene (0.77 ml; 7.1 mmol), ethyldiisopropylamine (0.61 ml; 3.5 mmol), palladacycle (66 mg; 0.70 mmol) and dioxane (10 ml) was stirred at 100° C. for 15 hours. Aqueous sodium hydroxide (10 ml; 4M) was added. The mixture was extracted with dichloromethane (3×20 ml). Chromatography on silica gel with dichloromethane, 10% methanol and 1% aqueous ammonia as solvent gave the title compound as an oil. Yield 0.12 g (11%). The corresponding salt was obtained by addition of a diethyl ether and methanol mixture (9:1) saturated with fumaric acid. Mp. 196.7-197.9° C.

4-[6-(4-Amino-phenylethynyl-pyridazin-3-yl]-1,4-diaza-bicyclo[3.2.2]nonane free base (Compound B2)

The title compound was prepared according to Method B. Mp. 181.7-183.4° C.

4-[6-(3-Fluoro-phenylethynyl)-pyridazin-3-yl]-1,4-diaza-bicyclo[3.2.2]nonane fumaric acid salt (Compound B3)

The title compound was prepared according to Method B. Mp. 173.5-175.0° C.

4-[6-(4-Methoxy-phenylethynyl)-pyridazin-3-yl]-1,4-diaza-bicyclo[3.2.2]nonane fumaric acid salt (Compound B4)

The title compound was prepared according to Method B. Mp. 208-209° C.

4-[6-(3-Pyridinylethynyl)-pyridazin-3-yl]-1,4-diaza-bicyclo[3.2.2]nonane fumaric acid salt (Compound B5)

The title compound was prepared according to Method B. Mp. 177.8-181.2° C.

Method C 4-(6-Phenylsulfanyl-pyridazin-3-yl)-1,4-diaza-bicyclo[3.2.2]nonane fumaric acid salt (Compound C1)

A mixture of 4-(6-chloropyridazin-3-yl-1,4-diazabicyclo[3.2.2]nonane (0.27 g; 1.1 mmol) thiophenol (0.96 g; 8.4 mmol), caesium carbonate (369 mg; 1.1 mmol) and DMF (1 ml) was stirred at 125° C. for 15 hours. Aqueous sodium hydroxide (5 ml; 4M) was added. The mixture was extracted with dichloromethane (3×5 ml). Chromatography on silica gel with dichloromethane, 10% methanol and 1% aqueous ammonia as solvent gave the title compound as an oil. Yield 0.32 g (93%). The corresponding salt was obtained by addition of a diethyl ether and methanol mixture (9:1) saturated with fumaric acid. Mp. 102.2° C.

4-(6-Phenylsulfinyl-pyridazin-3-yl)-1,4-diaza-bicyclo[3.2.2]nonane fumaric acid salt (Compound C2)

The title compound was prepared from 4-(6-phenylsulfanyl-pyridazin-3-yl)-1,4-diaza-bicyclo[3.2.2]-nonane by oxidation with MCPBA in chloroform, followed reduction using $PPh_3$ in dioxane at reflux. Mp. 162° C.

4-(6-Phenoxy-pyridazin-3-yl)-1,4-diaza-bicyclo[3.2.2]nonane fumaric acid salt (Compound C3)

The title compound was prepared according to Method C, using NaH as base, palladacycle (5%) and copper (5 eq.) at 160° C. for 10 days. Mp. 146-156° C.

Method D 4-(5-Benzylsulfanyl-[1.3.4]-thiadiazol-3-yl)-1,4-diaza-bicyclo[3.2.2]nonane fumaric acid salt (Compound D1)

A mixture of 1,4-diazabicyclo[3.2.2]nonane (1.0 g; 7.9 mmol), 2,5-bis-benzylsulfany[1.3.4]thiadiazole and ethyldiisopropylamine (2.8 ml; 15.8 mmol) was stirred at 110° C. for 15 hours. Mp. 138.1-139.2° C.

Method E

1-[4-(1,4-Diaza-bicyclo[3.2.2]non-4-yl)-phenyl]-3-phenyl-urea free base (Compound E1)

A mixture of 4-(1,4-diaza-bicyclo[3.2.2]non-4-yl)-phenylamine (0.43 g, 2.0 mmol), phenylisocyanate (0.29 ml, 2.5 mmol) and methanol (60 ml) was stirred at room temperature for 40 hours. The mixture was evaporated and diethylether (30 ml) was added, the precipitate was filtered. The product was isolated. Yield 0.23 g (34%). Mp. 145° C. (dec).

4-(4-Nitro-phenyl)-1,4-diaza-bicyclo[3.2.2]nonane hydrofluoric acid salt (Intermediate compound)

A mixture of 1,4-diazabicyclo[3.2.2]nonane (20.2 g, 160 mmol), 1-fluoro-4-nitrobenzene (17.5 ml, 163.3 mmol) and ethylene glycol diethyl ether (160 ml) was stirred at 135° C. for 18 hours. The mixture was cooled to room-temperature and diethyl ether (100 ml) was added. The mixture was filtered and the product was isolated by filtration. Yield 24.8 g (58%). Mp. 122-129° C.

4-(5-Nitro-pyridin-2-yl-1,4-diaza-bicyclo[3.2.2] nonane (Intermediate compound)

1,4-diazabicyclo[3.2.2]nonane (6.3 g, 50 mmol) was added to a mixture of 2-chloro-nitropyridine (11.9, 75 mmol), and dioxane (250 ml) at 0° C. The reaction mixture was allowed to reach room temperature. Water (100 ml) was added. The mixture was extracted with dichloromethane (3×50 ml). Chromatography on silica gel with dichloromethane and 10% methanol as solvent gave the title compound as an oil. Yield 8.1 g (65%). Mp. 143-146° C.

Method F 4-(1,4-Diaza-bicyclo[3.2.2]non-4-yl)-phenylamine (Intermediate compound)

A mixture of 4-(4-nitrophenyl)-1,4-diaza-bicyclo[3.2.2] nonane (0.50 g, 2.0 mmol), palladium on carbon (100 mg, 10%) and methanol (60 ml) was stirred for 15 minutes under hydrogen (130 ml of hydrogen was consumed). The crude mixture was filtered through celite and the product was isolated as an oil in quantitative yield.

2-Amino-N-[4-(1,4-diaza-bicyclo[3.2.2]non-4-yl) phenyl]-benzamide hydrochloric acid salt (Compound F1)

Was prepared according to Method F from N-[4-(1,4-diaza-bicyclo[3.2.2]non-4-yl)-phenyl]-2-nitro-benzamide. Mp. 238° C. (decomp.).

3-Amino-N-[4-(1,4-diaza-bicyclo[3.2.2]non-4-yl) phenyl]-benzamide hydrochloric acid salt (Compound F2)

Was prepared according to Method F from N-[4-(1,4-diaza-bicyclo[3.2.2]non-4-yl)-phenyl]-3-nitro-benzamide. Mp. >250° C. (decomp.).

4-Amino-N-[4-(1,4-diaza-bicyclo[3.2.2]non-4-yl)-phenyl]-benzamide hydrochloric acid salt (Compound F3)

Was prepared according to Method F from N-[4-(1,4-diaza-bicyclo[3.2.2]non-4-yl)-phenyl]-4-nitro-benzamide. Mp. >250° C. (decomp.).

4-Amino-N-[6-(1,4-diaza-bicyclo[3.2.2]non-yl)-pyridin-3-yl]-benzamide hydrochloric acid salt (Compound F4)

Was prepared according to Method F from N-[6-(1,4-diaza-bicyclo[3.2.2]non-4-yl)-pyridin-3-yl]-4-nitro-benzamide. Mp. >272° C. (decomp.).

3-Amino-N-[6-(1,4-diaza-bicyclo[3.2.2]non-4-yl)-pyridin-3-yl]-benzamide hydrochloric acid salt (Compound F5)

Was prepared according to Method F from N-[6-(1,4-diaza-bicyclo[3.2.2]non-4-yl)-pyridin-3-yl]-3-nitro-benzamide. Mp. >244° C. (decomp.).

6-(1,4-Diaza-bicyclo[3.2.2]non-4-pyridin-3-ylamine (Intermediate compound)

Was prepared according to Method F.

4-Amino-N-[4-(1,4-diaza-bicyclo[3.2.2]non-4-yl) phenyl]-benzenesulfonamide hydrochloric acid (Compound F6)

Was prepared according to Method F from N-[4-(1,4-Diaza-bicyclo[3.2.2]nonyl)-phenyl]-4-nitro-benzene-sulfonamide. Mp. >265° C.

Method G

N-[4-(1,4-Diaza-bicyclo[3.2.2]non-4-phenyl]benzamide hydrochloric acid salt (Compound G1)

4-(1,4-Diaza-bicyclo[3.2.2]non-4-yl)phenylamine (0.76 g, 3.5 mmol), benzoyl chloride (0.41 g, 3.5 mmol) and dichloromethane (33 ml) was stirred at room temperature for 17 hours. The mixture was evaporated and triturated with diethyl ether (50 ml). The crystals were recrystallised from methanol (40 ml). The hydrochloric acid salt was isolated. Yield 0.54 g (44%). Mp. 260° C. (decomp.).

N-[4-(1,4-Diaza-bicyclo[3.2.2]non-4-yl)phenyl]-2-nitro-benzamide hydrochloric acid salt (Compound G2)

Was prepared by Method G from 4-(1,4-Diaza-bicyclo [3.2.2]non-4-yl)phenylamine and 2-nitrobenzoyl chloride. Mp. >280° C.

N-[4-(1,4-Diaza-bicyclo[3.2.2]non-4-yl)-phenyl]-3-nitro-benzamide hydrochloric acid salt (Compound G3)

Was prepared by Method G from 4-(1,4-Diaza-bicyclo [3.2.2]non-4-yl)-phenylamine and 3-nitrobenzoyl chloride. Mp. >280° C.

N-[4-(1,4-Diaza-bicyclo[3.2.2]non-4-yl)phenyl]-4-nitro-benzamide hydrochloric acid salt (Compound G4)

Was prepared by Method G from 4-(1,4-diaza-bicyclo [3.2.2]non-4-yl) phenylamine and 4-nitrobenzoyl chloride. Mp. >280° C.

N-[4-(1,4-Diaza-bicyclo[3.2.2]non-4-41)-phenyl]-3-methoxy-benzamide hydrochloric acid salt (Compound G5)

Was prepared by Method G from 4-(1,4-diaza-bicyclo [3.2.2]nonyl)-phenylamine and 3-methoxybenzoyl chloride. Mp. 260° C.

N-[4-(1,4-Diaza-bicyclo[3.2.2]non-4-yl)-phenyl]-
benzenesulfonamide free base (Compound G6)

Was prepared by Method G from 4-(1,4-diaza-bicyclo[3.2.2]non-4-yl)-phenylamine and phenylsulfonyl chloride. Mp. 267° C.

N-[4-(1,4-Diaza-bicyclo[3.2.2]non-4-yl)-phenyl]-4-
methoxy-benzamide hydrochloric acid salt (Compound G7)

Was prepared by Method G from 4-(1,4-diaza-bicyclo[3.2.2]nonyl)phenylamine and 4-methoxybenzoyl chloride. Mp. >275° C.

N-[4-(1,4-Diaza-bicyclo[3.2.2]non yl)-phenyl]-3-
cyano-benzamide hydrochloric acid salt (Compound G8)

Was prepared by Method G from 4-(1,4-diaza-bicyclo[3.2.2]non yl)-phenylamine and 3-cyanobenzoyl chloride. Mp. 250° C. (decomp.).

N-[4-(1,4-Diaza-bicyclo[3.2.2]nonyl)-phenyl]1-cy-
ano-benzamide hydrochloric acid salt (Compound G9)

Was prepared by Method G from 4-(1,4-diaza-bicyclo[3.2.2]non-4-yl)-phenylamine and 4-cyanobenzoyl chloride. Mp. 250° C. (decomp.).

N-[4-(1,4-Diaza-bicyclo[3.2.2]non-4-yl)-phenyl]-3-
fluoro-benzamide hydrochloric acid salt (Compound G10)

Was prepared by Method G from 4-(1,4-diaza-bicyclo[3.2.2]non-4-yl)-phenylamine and 3-fluorobenzoyl chloride. Mp. >270° C. (decomp.).

N-[4-(1,4-Diaza-bicyclo[3.2.2]non-4-yl)-phenyl]-4-
fluoro-benzamide hydrochloric acid salt (Compound G11)

Was prepared by Method G from 4-(1,4-diaza-bicyclo[3.2.2]non-4-yl)-phenylamine and 4-fluorobenzoyl chloride. Mp. >270° C. (decomp.).

N-[4-(1,4-Diaza-bicyclo[3.2.2]non-4-yl)-phenyl]-2-
fluoro-benzamide hydrochloric acid salt (Compound G12)

Was prepared by Method G from 4-(1,4-diaza-bicyclo[3.2.2]non-4-yl)-phenylamine and 2-fluorobenzoyl chloride. Mp. >268° C. (decomp.).

N-[6-(1,4-Diaza-bicyclo[3.2.2]non-4-yl)-pyridin-3-
yl]-benzamide hydrochloric acid salt (Compound G13)

Was prepared according to Method G from 6-(1,4-diaza-bicyclo[3.2.2]non-4-yl)-pyridin-3-ylamine. Mp. 285° C. (decomp.).

1-[6-(1,4-Diaza-bicyclo[3.2.2]non-4-yl)-pyridin-3-
yl]-3-(2-nitrophenyl)-urea-1-N-oxide (Compound G14)

Was prepared according to Method G from 6-(1,4-diaza-bicyclo[3.2.2]non-4-yl)-pyridin-3-ylamine and 2-nitrophenylisocanate. Mp. 139° C. (decomp.).

1-[6-(1,4-Diaza-bicyclo[3.2.2]non-4-yl)-pyridin-3-
yl]-3-phenyl-urea hydrochloric acid salt (Compound G15)

Was prepared according to Method G from 6-(1,4-diaza-bicyclo[3.2.2]non-4-yl-pyridin-3-ylamine and phenylisocyanate. Mp. 235° C. (decomp.).

N-[6-(1,4-Diaza-bicyclo[3.2.2]non-4-yl)-pyridin-3-
yl]-4-nitro-benzamide hydrochloric acid salt (Compound G16)

Was prepared according to Method G from 6-(1,4-diaza-bicyclo[3.2.2]non-4-yl)-pyridin-3-ylamine and 4-nitrobenzoyl chloride. Mp. >310° C. (decomp.).

N-[6-(1,4-Diaza-bicyclo[3.2.2]non-4-pyridin-3-yl]-
3-nitrobenzamide hydrochloric acid salt (Compound G17)

Was prepared according to Method G from 6-(1,4-diaza-bicyclo[3.2.2]non-4-yl)-pyridin-3-ylamine and 3-nitrobenzoyl chloride. Mp. >280° C. (decomp.).

N-[4-(1,4-Diaza-bicyclo[3.2.2]non-4-yl)-phenyl]-4-
nitro-benzenesulfonamide hydrochloric acid salt (Compound G18)

Was prepared according to Method G from 6-(1,4-diaza-bicyclo[3.2.2]non-4-yl)-pyridin-3-ylamine and 4-nitrophenylsulfonyl chloride. Mp. >300° C. (decomp.).

N-[6-(1,4-Diaza-bicyclo[3.2.2]non-4-yl)-pyridin-3-
yl]-3-methoxy-benzamide hydrochloric acid salt (Compound G19)

Was prepared according to Method G from 6-(1,4-diaza-bicyclo[3.2.2]non-4-yl)pyridin-3-ylamine and 3-methoxybenzoyl chloride. Mp. >265° C. (decomp.).

N-[6-(1,4-Diaza-bicyclo[3.2.2]non-4-yl)-pyridin-3-
yl]-3-cyano-benzamide hydrochloric acid salt (Compound G20)

Was prepared according to Method G from 6-(1,4-diaza-bicyclo[3.2.2]non-4-yl)-pyridin-3-ylamine and 3-cyanobenzoyl chloride. Mp. >265° C. (decomp.).

N-[6-(1,4-Diaza-bicyclo[3.2.2]non-4-yl)-pyridin-3-
yl]-4-cyano-benzamide hydrochloric acid salt (Compound G21)

Was prepared according to Method G from 6-(1,4-diaza-bicyclo[3.2.2]non-4-yl)-pyridin-3-ylamine and 4-cyanobenzoyl chloride. Mp. >300° C.

Method H

2-Acetylamino-N-[4-(1,4-diaza-bicyclo[3.2.2]non-4-
yl)-phenyl]-benzamide free base (Compound H1)

Acetic acid (2 ml) was added to a mixture of 2-Amino-N-[4-(1,4-diaza-bicyclo[3.2.2]non-4-yl)-phenyl]-benzamide hydrochloric acid salt (365 mg, 1.1 mmol), sodium acetate (4.4 g, 54.2 mmol) and water (100 ml) at 0° C. The mixture was made alkaline by adding saturated sodium bicarbonate (20 ml). The mixture was extracted with ethyl acetate (3×50 ml). The product was isolated. Yield 95 mg (23%). Mp. 191° C.

3-Acetylamino-N-[4-(1,4-diaza-bicyclo[3.2.2]non-4-yl)phenyl]-benzamide free base (Compound H2)

Was prepared according to Method H. Mp. 184-187° C.

4-Acetylamino-N-[4-(1,4-diaza-bicyclo[3.2.2]non-4-yl-4)-phenyl]-benzamide free base (Compound H3)

Was prepared according to Method H. Mp. >240° C.

4-Acetylamino-N-[6-(1,4-diaza-bicyclo[3.2.2]non-4-yl)-pyridin-3-yl]-benzamide free base (Compound H4)

Was prepared according to Method H. Mp. 255° C. (decomp.).

3-Acetylamino-N-[6-(1,4-diaza-bicyclo[3.2.2]nonyl)-pyridin-3-yl]-benzamide free base (Compound H5)

Was prepared according to Method H. Mp. 60° C.

Example 2

In Vitro Inhibition of $^3$H-α-Bungarotoxine Binding in Rat Brain

In this example the affinity of the compounds of the invention for binding to $\alpha_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist. $^3$H-α-Bungarotoxine labels nicotinic acetylcholine receptors formed by the $\alpha_7$ subunit Isoform found in brain and the $\alpha_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of Ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an IC$_{50}$ (the concentration of the test substance which inhibits the specific binding of $^3$H-α-bungarotoxin by 50%).

The results of these experiments are presented in Table 1 below.

TABLE 1

| Inhibition of $^3$H-α-Bungarotoxine Binding | |
|---|---|
| Compound No. | IC$_{50}$ (μM) |
| B1 | 0.060 |
| B4 | 0.18 |
| B5 | 0.15 |
| C1 | 0.60 |

The invention claimed is:

1. A diazabicyclic aryl derivative represented by Formula I

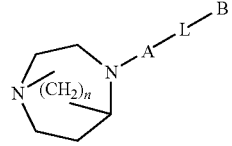

any of its enantiomers or any mixture of its enantiomers, or a pharmaceutically acceptable salt thereof, wherein n is 2; and A represents a pyridine group;

B represents a phenyl group, optionally substituted with substituents selected from the group consisting of alkyl, cycloalkyl, hydroxyl, alkoxy, cyanoalkyl, halo, trihaloalkyl, trihaloalkoxy, cyano, amino, nitro and —NH(CO)-alkyl; and L represents —NH(CO)NH—.

2. The diazabicyclic aryl derivative of claim 1, any of its enantiomers or any mixture of its enantiomers, or a pharmaceutically acceptable salt thereof, wherein B represents a phenyl group, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl.

3. The diazabicyclic aryl derivative of claim 1, which is

1-[6-(1,4-Diaza-bicyclo[3.2.2]non-4-yl)-pyridin-3-yl]-3-(2-nitro-phenyl)-urea-1-N-oxide;

1-[6-(1,4-Diaza-bicyclo[3.2.2]non-4-yl)-pyridin-3-yl]-3-phenyl-urea;

or any of its enantiomers or any mixture of its enantiomers, or a pharmaceutically acceptable salt thereof.

4. A pharmaceutical composition comprising a therapeutically effective amount of an diazabicyclic aryl derivative of claim 1, any of its enantiomers or any mixture of its enantiomers, or a pharmaceutically-acceptable addition salt thereof, together with at least one pharmaceutically-acceptable carrier or diluent.

* * * * *

UNITED STATES PATENT AND TRADEMARK OFFICE
CERTIFICATE OF CORRECTION

PATENT NO.      : 7,662,808 B2                        Page 1 of 1
APPLICATION NO. : 10/586836
DATED           : February 16, 2010
INVENTOR(S)     : Peters et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 577 days.

Signed and Sealed this

Thirtieth Day of November, 2010

David J. Kappos
*Director of the United States Patent and Trademark Office*